United States Patent [19]

Furkert

[11] 4,054,562
[45] * Oct. 18, 1977

[54] PROCESS FOR THE MANUFACTURE OF LACTAMS

[75] Inventor: Herbert Furkert, Grosskonigsdorf, Germany

[73] Assignee: Davy Powergas GmbH, Cologne, Germany

[*] Notice: The portion of the term of this patent subsequent to Sept. 25, 1990, has been disclaimed.

[21] Appl. No.: 261,219

[22] Filed: June 9, 1972

[30] Foreign Application Priority Data

June 18, 1971 Germany .................. 2130036

[51] Int. Cl.² .................................. C07D 201/04
[52] U.S. Cl. .................. 260/239.3 A; 423/356; 423/387; 423/525; 423/530; 423/541 A
[58] Field of Search .............. 260/239.3 A; 423/356, 423/387, 525, 530, 541

[56] References Cited

U.S. PATENT DOCUMENTS

| | | | |
|---|---|---|---|
| 2,221,369 | 11/1940 | Cass | 260/239.3 A |
| 3,133,055 | 5/1964 | Grulet et al. | 260/239.3 A |
| 3,275,407 | 9/1966 | Furkert et al. | 423/356 |
| 3,292,996 | 12/1966 | Furkert et al. | 423/356 |
| 3,321,275 | 5/1967 | Furkert et al. | 423/356 |
| 3,359,069 | 12/1967 | Furkert et al. | 423/541 |
| 3,383,170 | 5/1968 | Furkert et al. | 423/541 |
| 3,701,809 | 10/1972 | De Rooij et al. | 423/387 |
| 3,761,575 | 9/1973 | Furkert | 423/356 |
| 3,795,731 | 3/1974 | Furkert | 423/351 |
| 3,852,272 | 12/1974 | De Rooij | 260/239.3 A |
| 3,852,273 | 12/1974 | De Rooij | 260/239.3 A |

OTHER PUBLICATIONS

Sittig, "Caprolactam and Higher Lactams" (Noyes Development Corp.), p. 70, (1966).
Seel "Fortschr. Chem. Forsch" vol. 4, pp. 301-332 (1963).

*Primary Examiner*—Henry R. Jiles
*Assistant Examiner*—Robert T. Bond
*Attorney, Agent, or Firm*—Millen & White

[57] ABSTRACT

In a process for manufacturing a lactam which includes rearranging a cycloalkanone-oxime with sulfuric acid to form the lactam, neutralizing the rearrangement mixture with ammonia to form ammonium sulfate, and separating the lactam and the ammonium sulfate, the improvement which comprises:

a. heating at least a portion of the ammonium sulfate to a temperature of 240° – 460° C to form ammonia and ammonium bisulfate;
b. separating the ammonia from the ammonium bisulfate;
c. recycling the ammonia to neutralize the rearrangement mixture;
d. burning the ammonium bisulfate at a temperature of 850° – 1250° C to form an $SO_2$-containing gas;
e. oxidizing the $SO_2$-containing gas to form sulfuric acid; and
f. recycling the sulfuric acid to the rearrangement stage.

18 Claims, 1 Drawing Figure

PROCESS FOR THE MANUFACTURE OF SPIRO COMPOUNDS OF THE STEROID SERIES

The present invention provides a novel process for the manufacture of steroid-17-spiro-(2'-oxacycloalkanes), in particular of those wherein the heterocyclic oxygen atom is in 17β-position.

The novel process of the present invention has in particular for its object the manufacture of 17-spiro-(2'-oxacyclopentane) compounds of the general formula

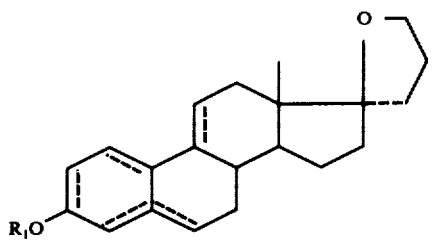

(I)

wherein $R_1$ represents a hydrogen atom or a lower alkyl group, which contain a double bond in 5-position and a methyl group in 10-position or three double bonds in the positions 1,3 and 5(10), and which can contain an additional double bond in the 9(11)-position.

These compounds are particularly useful intermediates for obtaining known therapeutically useful compounds or new analogs thereof.

Thus, for example, a number of compounds with the 17-spiro-(2'-oxacyclopentane) grouping can be used for antagonising the aldosterone action, cf. G. E. Arth et al., J. Med. Chem. 6, 617–618 (1963) (reference A). Other compounds with this grouping are characterised by anti-estrogenic and implantation-inhibiting action, cf. G. E. Arth: U.S. Pat. No. 3,798,213 (reference B). The compounds of the present invention can be converted into the corresponding spirolactones by oxidation and are therefore important intermediates for obtaining these aldosterone antagonists, cf. G. F. Reynolds et al.; Tetrahedron Letters 1970, 5057–5059 (reference C).

It has hitherto been possible to obtain the compounds of the formula I, or further analogous 17-spiro-(2' -oxacyclopentane) compounds, by three synthetic routes all of which have in common the last step, the acid-catalysed cyclisation of a 17,21a-dihydroxy-21-homo-17α-pregnane grouping with toluene sulphochloride in pyridine. In each route, the necessary 17,21a-diol was obtained from a suitable 17-oxosteroid. In the method of reference A, the 17-oxosteriod was treated with a Grignard compound which was prepared from tetrahydropyranyl(2) ether of propargyl alcohol, whereupon the triple bond was selectively saturated and the tetrahydropyranyl protective group split off by hydrolysis. According to the method of reference B, the 17-oxosteroid is treated with allyl magnesium halide, the allyl double bond is hydroborated with bis-(3-methyl-2-butyl)-borohydride, and the trialkyl borane obtained as intermediate is treated with hydrogen peroxide. In method C, the lactone of a corresponding 17-hydroxy-17α-pregnane-C, the lactone of a corresponding 17-hydroxy-17α-pregnane-21-carboxylic acid is reduced with a complex metal hydride. The lactone is obtained from a corresponding 17-oxosteroid in known manner by a 4-step process: treatment with alkali metal acetylide, conversion into the ω-magnesium halide, carboxylation, and hydrogenation.

However, none of these three methods is suitable for an industrially economical use and especially for obtaining the desired compounds of the formula I. The method of reference C is hardly suitable in any case, because the starting materials are compounds which are generally desired as end products; and in addition, the entire process comprises 6 steps. Alone on account of the unavoidable use of the tetrahydropyranyl protective group, the method of reference A, which comprises 4 steps, offers fewer advantages, because the additional asymmetric carbon atom results in the formation of two epimers, which complicate the characterisation and separation of the product in the first and second reaction steps. Moreover, the hydrogenation of the triple bond must be carried out selectively if the 5(6)-dougle bond is to remain intact in the processed derivative (this also applies to the method of C). The method according to reference B, which ought to be superior to the others, since it comprises only 3 steps, is however even more impeded in its use by a 5(6)-double bond; the borinating reagent in the second step does not act selectively enough to leave the 5(6)-double bond intact in the course of the reaction with the allyl double bond. (What has been said here in respect of the 5(6)-dougle bond applies also to at least the same extent to the 9(11)-double bond which may or may not be present). Apart from this disadvantage, the total yield of the method is also low. According to experimental data (cf. B, Examples 9–11), the total yield of the process was only about 12.5% by weight, and in the 3-step process, it was necessary to carry out two chromatographic separations.

The final step which is common to the methods of A, B and C — the cyclisation — is also by no means unproblematical, although the reaction itself generally proceeds with good yields. The free hydroxyl group in 3-position, which may or may not be present in the starting material, is simultaneously co-tosylated. However, those skilled in the art will be aware that the liberation of the 3-hydroxyl group from the corresponding tosyloxy group can only be carried out by wasteful roundabout methods. The methods according to B and C, however, involve the use of reagents which liberate an esterified 3β-hydroxyl group, directly before the cyclisation discussed above. This circumstance detracts still further from their use for an economical manufacture of the compounds of the formula I.

It has now been found that, surprisingly, the removal of the tertiary amino group of a 17β-hydroxy-17-(γ-dilower alkylaminopropyl)-steroid results in the formation of an oxygen-containing spiro ring and not of the expected double bond. Since the amines required for this cyclisation can be obtained in one step direct from the corresponding 17-oxosteroids, this process constitutes by far the shortest synthetic route to yield the desired spiro compounds. Furthermore, the conditions under which the removal of the amino group takes place are such that neither double bonds nor free hydroxyl groups are attacked, with favourable consequences for both the yields and the purity of the final products.

The process of the invention comprises reacting a 17-oxosteroid of the general formula

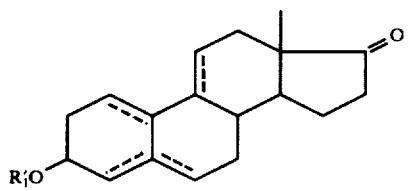

(II)

wherein R$_1$' represents a hydrogen atom, a lower alkyl group or an acyl group, which contains a double bond in 5-position and a methyl group in 10-position, or three double bonds in the positions 1,3 and 5(10), and which can contain an additional double bond in the position 9(11), with an organometallic compound of the formula

R$_o$—(CH$_2$)$_3$—M     (III)

wherein M represents a grouping MgX, in which X is a halogen atom or represents an alkali metal atom, and R$_o$ represents a di-lower alkylamino group, and deaminating the resultant 17β-hydroxy-17α-(γ-di-lower alkylaminopropyl) compound of the general formula

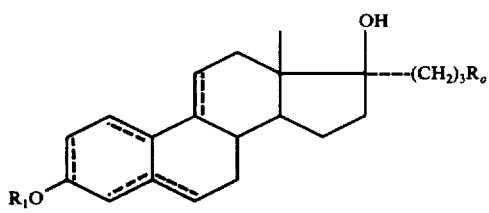

(IV)

wherein R$_o$ and R$_1$ are as defined hereinbefore, which contains double bonds and optionally the methyl group in the positions referred to above, with simultaneous cyclisation.

Unless otherwise indicated, the term "lower" used to qualify an organic group means that such group contains at most 7, but preferably 1 to 4, carbon atoms.

A lower alkyl group is, for example, a n-propyl, isopropyl, n-butyl, sec.butyl, tert.butyl group, a branched or peferably linear pentyl, hexyl or heptyl group, especially an ethyl group and, most preferably, a methyl group.

An acyl group represented by R$_1$' is derived in particular from the carboxylic acids common in steroid chemistry, for example monocarboxylic acids containing at most 18 carbon atoms, such as aliphatic carboxylic acids, in particular formic acid or a lower alkanecarboxylic acid whose lower alkyl group is one of those referred to hereinabove, primarily propionic, butyric, isobutyric, valeric, isovaleric, enanthic and diethylacetic acid, and above all capronic, trimethylacetic and acetic acid; halogenated lower alkanecarboxylic acids, such as chloroacetic acid, trichloroacetic or trifluoroacetic acid; aromatic carboxylic acids, for example benzoic acids which are unsubstituted or substituted by halogen, such as fluorine, chlorine or bromine atoms, by hydroxyl groups, lower alkoxy groups, such as methoxy or ethoxy groups, lower alkyl groups, for example those referred to hereinbefore, or by nitro groups. Also suitable are corresponding dicarboxylic acids which contain at most 12 carbon atoms, for example succinic acid, glutaric acid, adipic acid and phthalic acid.

The additional 9(11)-double bond is preferably present in those compounds which contain the 5(6)-double bond besides the 10-methyl group.

The substituents of the di-lower alkylamino group R$_o$ can be the same or dissimilar. The di-lower alkylamino group R$_o$ is preferably the diethylamino, methylethylamino, methyl- propylamino, ethyl-propylamino, dipropylamino or dibutylamino group. Most preferably, however, this amino group is the dimethylamino group.

Where M in formula III represents an alkali metal atom, it is, for example, a sodium or potassium atom or preferably the lithium atom. Together with the monohalogenated magnesium atom, the γ-di-lower alkylaminopropyl group can also form a Grignard reagent, i.e. a γ-di-lower alkylaminopropyl magnesium halide, for example an iodide or chloride or in particular a bromide. However, the particularly preferred reagent is γ-dimethylaminopropyl lithium.

The reaction of the 17-oxosteroids of the formula II is carried out in known manner under conditions which are customary in organometallic or Grignard reactions. The process is carried out mainly under anhydrous conditions in an aprotic solvent or diluent, for example in an ether, such as diethyl ether, diisopropyl ether, ethylene glycol dimethyl ether, diethylene glycol dimethyl ether, tetrahydropyrane or, most preferably, tetrahydrofurane, or in a hydrocarbon, in particular an aromatic monocyclic hydrocarbon, such as benzene, toluene or one of the xylenes, or in a mixture of these solvents. Preferably the complex which is formed in the first stage is decomposed by hydrolysis, for which water, an aqueous solution of sodium chloride, or advantageously an aqueous ammonium chloride solution is used. It is even more advantageous to carry out the hydrolysis by using an aqueous solution of an acid, for example an inorganic acid, such as sulphuric acid, phosphoric acid or a hydrohalic acid, in particular hydrochloric acid, or a water-miscible organic acid, for example one of the carboxylic acids cited hereinbefore, in particular a lower aliphatic carboxylic acid, and above all, acetic acid. The liberated desired reaction product is converted in the acid medium into a corresponding acid addition salt. In this form it remains in solution in the aqueous phase and can be readily separated from neutral reaction components by extraction, whereby on the one hand, a simple purification of the product, and on the other, an easy recovery of any unreacted starting material, is attained.

The acid addition salts of the di-lower alkylaminopropyl steroids of the formula IV can be converted in known manner, for example with alkalies or ion exchangers, into the free bases.

If the starting material contains an esterified 3-hydroxyl group, i.e. if R$_1$' in formula II represents an acyl group, then this group is liberated during the reaction with the organometallic reagent.

The second step of the process of this invention, the deamination with cyclisation, takes place under the general conditions which are customary for removing the tertiary amino group, i.e. by thermal decomposition of the compounds of the formula IV in the form of their quaternary bases.

The reaction is carried out under the known conditions of the Hofmann elimination by converting the di-lower alkylamino compound into the corresponding quaternary tri-lower alkyl ammonium salt and decomposing this latter by heat in the form of the corresponding quaternary base. A suitable quaternary agent is a di-lower alkyl sulphate or especially a lower alkyl halide, for example a lower alkyl chloride, lower alkyl bromide and preferably a lower alkyl iodide. The particularly preferred lower alkyl group in these quaternising agents is the methyl group. The quaternisation is carried out in an excess of alkylating agent, or advantageously in an orgnic solvent, in particular a lower alkanol, preferably methanol, but also in acetone, methyl ethyl ketone or ethyl acetate. The quaternary base is liberated from the corresponding salt by using a strong base. For this purpose strong basic ion exchangers, silver hydroxide, thallium (I) hydroxide, and preferably alkali metal hydroxides, such as sodium and potassium hydroxide, are used. If the alkylating agent is a sulphate it is also possible to use barium hydroxide. Water is used as solvent or diluent, if appropriate in the presence of an organic water-miscible solvent, for example an alcohol, such as a lower alkanol, a lower glycol or glycerol. But it is also possible to liberate the base with a potassium or particularly a sodium alcoholate, for example one that is derived from the alcohols just mentioned. The thermolysis (thermal decomposition) is carried out, for example, by concentrating a solution of the quaternary base at increasing temperature and, if appropriate, under reduced pressure, and, if necessary, heating it further up to the point of decomposition, for example to 200° C. A particularly advantageous modification consists in treating the quaternary salt with an equivalent amount of an alkali metal hydroxide in aqueous solution, adding ethylene glycol, and concentrating the mixture by slow distillation until decomposition is complete. Upon cooling, the product crystallises out in great purity. It is advisable to work with free quaternary bases only when carefully excluding atmospheric carbon dioxide.

In a particularly preferred embodiment of the process of the invention the 3β-hydroxy-androst-5en-17-one, or a lower aliphatic carboxylic acid ester thereof, for example an ester of one of the carboxylic acids previously referred to herein, in particular its acetate, is treated with γ-dimethylaminopropyl lithium and the 17α-(γ-dimethylaminopropyl)-androst-5-en-3β,17β-diol obtained is subsequently thermolysed in the form of its quaternary hydroxide, which has been obtained by quaternisation with methyl iodide and liberation of the base from the methoiodide with an equimolar amount of sodum hydroxide. The thermolysis is preferably carried out in aqueous ethylene glycol, and the product crystallises out virtually pure direct from the reaction mixture. The resultant product of the formula

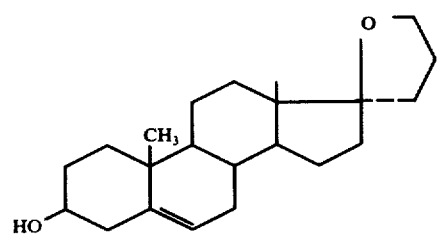

(IA)

is of key importance as a useful starting material for all steroids with the 2'-spiro-2',3'α-tetrahydrofuran ring. However, its technical use has up to now been impeded by the difficulty in obtaining it (cf. the synthetic routes discussed at the outset, in particular reference C). In the process of the invention, this compound is obtained readily in a total yield of 70% by weight, referred to the consumed starting 17-oxosteroid. the process of the invention proceeds analogously in respect of the 9(11) compounds. Another especially preferred starting material is estron methyl ether (3-methoxyestra-1,3,5(10)-trien-17-one), which is also advantageously processed under the preferred conditions referred to previously.

The end products of the formula I can be converted into the therapeutically active spiro steroids by methods conventionally employed in steroid chemistry, for example by dehydrogenating a free hydroxyl group to give the oxo group, for example converting the Δ⁵-3β-hydroxyl grouping into the Δ⁴-4-keto grouping, introducing one or more double bonds, for example into the positions 1 and 6, or saturating the existing double bonds by reduction, adding a methylene or difluoromethylene bridge to a double bond, adding a thiocarboxylic acid to a double bond, in particular the 6(7)-double bond, or oxidising the methylene group adjacent to the oxygen atom to give the carbonyl group in the tetrahydrofuran ring. A number of typical uses are described in the following Examples, in particular the manufacture of the hitherto unknown 2',3'-α-tetrahydrofuran-2'-spiro-17[androsta-4,6,9(11)-trien-3one].

The present invention also comprises the 17β-hydroxy-17α-(γ-di-lower alkylaminopropyl)-steroids obtained as intermediates as well as the process for their manufacture described hereinbefore. Particularly preferred compounds are those of the general formula

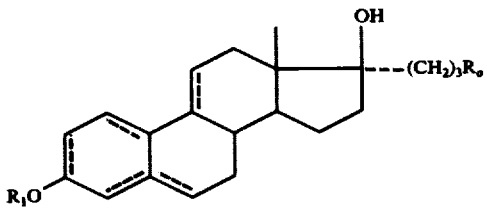

(IV)

wherein R₀ represents a di-lower alkylamino group and R₁ represents a hydrogen atom or a lower alkyl group, which contain a double bond in 5-position and a methyl group in 10-position, or three double bonds in the positions 1,3 and 5(10), and which can contain an additional double bond in the 9(11)-position, and also addition salts of these compounds.

Of these compounds, in particular 17α-(γ-dimethylaminopropyl)-androst-5en3β, 17β-diol, 17α-(γ-dimethylaminopropyl)-androsta-5,9(11)-dien-3β,17β-diol and 17α-(γ-dimethylaminopropyl)-3methoxy-estra-1,3,5(10)-trien-17β-ol and their methoiodides are suitable for the further conversion according to the invention.

By the addition salts of the compounds of formula IV of the present invention are meant, on the one hand, acid addition salts, and on the other, quaternary salts, for example methosalts. The former are obtained by addition of an organic or inorganic acid, preferably one of those suitable for the formation of therapeutically or industrially useful salts, to the tertiary amino group. Examples of such acids are: hydrohalic acids, sulphuric acids, phosphoric acids, nitric acid, aliphatic, carbocyclic, aromatic or heterocyclic carboxylic or sulphonic acids, for example formic acid, acetic acid, propionic acid, succinic acid, glycollic acid, lactic acid, malic acid, tartaric acid, citric acid, ascorbic acid, maleic acid, hydroxymaleic acid, pyruvic acid or levulinic acid; phenylacetic acid, benzoic acid, anthranilic acid, p- hydroxybenzoic acid, salicylic or p-aminosalicylic acid, mthanesulphonic, ethanesulphonic, hydroxyethanesulphonic and ethylenesulphonic acid; a halobenzenesulphonic acid, a toluenesulphonic acid, a naphthalenesulphonic acid or the sulphanilic acid, or an anthraquinonedisulphonic acid.

These or other acid addition salts of the compounds of this invention, for example the picrates or perchlorates, can also be used for purifying the free bases by converting the free bases into such salts, separating these and liberating the bases from them once more. On account of the close relationship between the compounds of this invention in the free form and in the form of their acid addition salts, what is stated throughout this specification in respect of the free bases refers also to the corresponding acid addition salts, wherever this applies.

By the addition salts referred to as quaternary salts are meant in particular those which are obtained by addition of a lower alkyl ester of a strong inorganic or organic acid to the tertiary amino group, whereby this is quaternised. Suitable ester-forming strong organic acids are in particular organic, for example aliphatic and carbocyclic, sulphonic acids, such as methanesulphonic, trifluoromethanesulphonic, camphorsulphonic, benzenesulphonic, p-bromobenzenesulphonic or toluenesulphonic acid. Organic acids to be mentioned in this connection are in particular sulphuric acid, perchloric acid and, primarily, the hydrohalic acids, especially hydrochloric and hydrobromic acid, above all hydroiodic acid. The lower alkyl group is preferably one of those referred to hereinbefore, in particular the methyl group, in which case these quaternary salts are called methosalts. The quaternary compounds of the invention are designated as salts of the corresponding 17α-(γ-tri-lower alkylammoniumpropyl)-steroids. The methoiodides mentioned as being preferred are also known as iodomethylates.

The invention also relates to those embodiments of the process in which a compound obtained in any stage of the process as an intermediate is used as starting material and the missing steps are carried out, or in which the process is discontinued at any stage, or in which the starting materials are formed under the reaction conditions, or in which a reaction component may be present in the form of its salts.

Those starting compounds which yield the compounds referred to as being preferred are principally used for the reactions of the present invention.

The 17-oxosteroids used as starting materials are known or they can be obtained by known methods.

The following Examples illustrate the invention in more detail without restricting it to what is described therein. Examples 1 to 3, 7, 8 and 12 to 15 relate to the process of the invention itself, whereas the remaining Examples illustrate a number of possible syntheses for obtaining known or new therapeutically active compounds.

EXAMPLE 1

A solution of 45.6 g of 3β-hydroxy-androst-5-en-17-one in 1120 ml of absolute tetrahydrofurane is cooled by external cooling to +2.5° C. Then 10 g of clean lithium wire cut into small pieces are added under nitrogen and 80 ml of 1-chloro-3-dimethylamino-propane are added dropwise at +2.5° C with very rapid stirring. As soon as the reaction temperature exceeds +5° C, the external cooling is intensified, so that the internal temperature of the reaction mixture rises to at most 15° C in the course of half an hour. The internal temperature is kept for a further half an hour at 10° to 12° C and thereafter two 10 ml portions of the chloroamino base are added at 10° to 12° C, with stirring in an atmosphere of nitrogen, at an interval of 25 minutes. The reaction mixture is stirred for 2¾ hours at room temperature and, after unreacted lithium has been filtered off, diluted with 4 liters of ice-cold aqueous acetic acid. Neutral by-products and unreacted starting material are extracted from this solution with ethyl acetate. The aqueous phase is made alkaline, with stirring, with 550 ml of 10 normal sodium hydroxide solution, whereupon the desired 17α-(γ-dimethylaminopropyl)-androst-5-en-3β-diol is obtained in crystalline form. The crystalline product is filtered off with suction, washed neutral with copious amounts of water and dried in vacuo at 50° C. A melting point of 17″°-181° C is obtained by a single additional crystallisation from methanol/water.

EXAMPLE 2

70 ml of methyl iodide are added at room temperature to a solution of 42 g of 17α-(γ-dimethylaminopropyl)-androst-5-en-3β,17β-diol in 420 ml of methanol. The quaternary methoiodide of the above amine [17α-(γ-trimethylammoniumpropyl)-androst-5-en-3β,17β-diol-iodide] crystallises out after a short time. After concentrating the reaction mixture, the product is filtered off and dried in vacuo at 60° C. Yield: 53.9 g; m.p. 288°-289° C (with decomp.). The above salt (10.3 g) is dissolved hot in 100 ml of methanol. To this solution are added 20 ml of normal aqueous sodium hydroxide and 100 ml of water and the mixture is heated to 65° C until a clear solution is obtained. Then 200 ml of ethylene glycol are added to the reaction mixture and the solvent is slowly distilled off until an internal temperature of app. 185° C is reached, which is then kept for 6 hours. Upon cooling, the 2′,3′-α-tetrahydrofuran-2′-spiro-17(androst-4en-3β-ol) crystallises out from the reaction solution. The crystals are filtered off with suction, washed with a small amount of ethylene glycol and copiously with water, and dried in vacuo at 60° C to constant weight. Yield: 5.86 g; m.p. 191°-193° C.

EXAMPLE 3

50 g of 17α-(γ-dimethylaminopropyl)-androst-5-en-3β,17β-diol are dissolved hot in 500 ml of methanol. The solution is then cooled to room temperature and treated with 85 ml of methyl iodide. The methoiodide precipitates after a short time. Then 500 ml of methanol are added and excess methyl iodide is removed by distilling off 500 ml of solvent. To the hot suspension are then added 135 ml of normal aqueous sodium hydroxide solution and 500 ml of water. The mixture is heated briefly and a clear solution is obtained at an internal temperature of app. 65° C. To this solution are added 1000 ml of ethylene glycol and the solvent is slowly distilled off until an internal temperature of 180°-185° C is attained. The trimethylamine begins to split off already at 110° C. 2′,3′-α-Tetrahydrofuran-2′ -spiro-17(androst-5-en-3β-ol) crystallises out on cooling the reaction solution to room temperature. The crystals are filtered off with suction, washed neutral with water and dried in vacuo at 60° C in a water jet vacuum.

Yield: 40.5 g; m.p. 191°-193° C.

EXAMPLE 4

20 g of 2',3'-α-Tetrahydrofuran-2'-spiro-17(androst-5-en-3β-ol) are dissolved in 1 liter of toluene and 180 ml of cyclohexanone and 300 ml of the solvent mixture are then distilled off. The reaction mixture is cooled and 25 g of aluminium isopropylate are added thereto. The mixture is refluxed for 30 minutes, then cooled, and 1 liter of saturated aqueous Seignette salt solution is added. The components of the crude mixture which are volatile with steam are removed by steam distillation and the residue is extracted with ethyl acetate. The organic phase is washed successively with dilute aqueous hydrochloric acid and saturated saline solution, dried over sodium sulphate and concentrated in a water jet vacuum. The crude product is chromatographed over silica gel and 17 g of 2',3'-α-tetrahydrofuran-2'-spiro-17(androst-4-en-3-one) are eluted with a mixture of toluene/ethyl acetate (9:1). Melting point 92°–93° C after recrystallization from acetone/petroleum ether.

EXAMPLE 5

A mixture of 5.35 g of 2',3'-α-tetrahydrofuran-2'-spiro-17(androst-4-en-3-one) and 3.75 g of chloranil is refluxed for 3 hours in 134 ml of methanol. The reaction mixture is diluted with methylene chloride and washed neutral repeatedly in succession with a solution of 3% sodium dithionite in 1-normal aqueous sodium hydroxide solution and with saturated aqueous solution of sodium chloride. The crude product obtained after drying and concentrating the methylene chloride phase is chromatographed over silica and 4.1 g of 2',3'-α-tetrahydrofuran-2'-spiro-17(androsta-4,6-dien-3-one) are eluted with a mixture of toluene/ethyl acetate. Melting point 97°–98° C after crystallation from acetone/hexane.

EXAMPLE 6

To a solution of 2 g of 2',3'-α-tetrahydrofuran-2'-spiro-17(androsta-4,6-dien-3-one) in 12 ml of methanol are added in succession 3 ml of water and 1 ml of thioacetic acid. The reaction mixture is stirred for 3 hours at room temperature, diluted with ethyl acetate and washed neutral in succession with 2-normal aqueous sodium bicarbonate solution and with saturated aqueous solution of sodium chloride. The crude product obtained after drying and concentrating the organic phase is recrystallised once from methanol, to yield 1.08 g of 2',3'-α-tetrahydrofuran-2'-spiro-17(7α-acetylthio-androst-4-en-3-one) with a melting point of 180°–182° C.

EXAMPLE 7

44 g of estrone-3-methyl ether are reacted in 1.5 liters of tetrahydrofuran with 10 g of lithium wire and a total amount of 100 ml of 1-chloro-3-dimethylamino-propane as in Example 1. Excess lithium is removed, and the reaction mixture is poured into 4 liters of 10% aqueous acetic acid and extracted with 3 × 1 liter of ethyl acetate. The ethyl acetate extracts are washed with a further 4 liters of 10% aqueous acetic acid and washed copiously with water until neutral, and concentrated in vacuo. 11.52 g of pure estrone-3-methyl ether are recovered from the resultant neutral portion (18 g) by one crystallisation from methylene chloride/ether. The acetic acid aqueous components of the batch are made alkaline with 1.4 liters of 10-normal aqueous sodium hydroxide solution and extracted with ether. The ethereal extracts are washed neutral with water, dried over sodium sulphate and evaporated in vacuo, to yield 26.7 g of 17α-(γ-dimethylaminopropyl)-3-methyl-estra-1,3,5(10)-trien-17β-ol, which melts at 110°–112° C after crystallisation from methylene chloride/ether/pentane.

EXAMPLE 8

A solution of 26.7 g of 17α-(γ-dimethylaminopropyl)-3-methoxy-estra-1,3,5(10)-trien-17β-ol in 240 ml of methanol is treated at room temperature with 42 ml of methyl iodide. After app. 1 hour the methoiodide of the starting base [17α-(γ-trimethylammoniumpropyl)-3-methoxy-estra-1,3,5(10)-trien-17β-ol-iodide] begins to crystallise out from the solution. The mixture is cooled to −10° C and kept thereat for 2 hours. The crystals are then filtered off with suction, washed with cold methanol (−10° C) and dried in vacuo. Yield: 30.85 g; m.p. 221°–223° C (with decomp.). The above salt (25.6 g) is heated in 250 ml of methanol with 50 ml of 1-normal aqueous NaOH and 250 ml of water, with a clear solution being obtained at a temperature of 54° C. Upon addition of 500 ml of ethylene glycol, a methanol/water mixture is distilled off until the temperature of the reaction mixture has reached 185° C after 3 hours. The reaction mixture is kept for a further 4 hours at this temperature, cooled, and allowed to stand overnight at room temperature, in the course of which the desired spiro ether crystallises out from the reaction solution. The crystals are subsequently filtered off with suction and 480 ml of ethylene glycol are recovered from the filtrate by vacuum distillation. The above crystals are taken up in ether and the ethereal solution is washed in succession twice with 2-normal aqueous hydrochloric acid, water, and saturated aqueous solution of sodium chloride, respectively, dried over sodium sulphate, and concentrated in vacuo. Crystallisation of the residue from ether yields 12.44 g of 2',3'-α-tetrahydrofuran-2'-17(3-methoxyestra-1,3,5(10)-triene) with a melting point of 118°–119° C.

EXAMPLE 9

With stirring at −70° C, 5 g of 2',3'-α-tetrahydrofurane-2-spiro-17(3-methoxy-estra-1,3,5(10)-triene) are added to a solution of 6 g of lithium in 400 ml of liquid ammonia. The reaction mixture is stirred for 1 hour at −70° C, treated with methanol, which must be initially added dropwise with caution, until the blue reaction solution turns colourless, and thereafter with 100 ml of water. The solution is warmed to room temperature, thereupon the bulk of the ammonia evaporates. The products is taken up in ethyl acetate, washed neutral with a saturated aqueous solution of sodium chloride, dried over sodiun sulphate and concentrated in vacuo, to yield 4.84 g of 2',3'-α-tetrahydrofurane-2'-spiro-17(3-methoxy-estra-2,5(10)-diene), which is crystallised from acetone/petroleum ether (yield: 3.70 g) and then melts at 96°–97° C.

EXAMPLE 10

A solution of 1 g of 2',3'-α-tetrahydrofurane-2'-spiro-17(3-methoxy-estra-2,5(10)-diene) in 100 ml of methanol is refluxed for 45 minutes with 20 ml of 2 normal aqueous hydrochloric acid and diluted with ethyl acetate. The solution is washed neutral with a saturated aqueous solution of sodium chloride, dried over sodium sulphate and concentrated in vacuo, to yield 0.91 g of 2',3'-α-tetrahydrofurane-2'-spiro-17(estra-4-en-3-one), which is crystallised from acetone/petroleum ether (yield: 0.73 g) and then melts at 122°–123° C.

EXAMPLE 11

A solution of 100 mg of 2',3'-α-tetrahydrofurane-2'-spiro-17(3-methoxyoestra-2,5-(10)-diene) in 5 ml of acetone is treated at room temperature with 40 mg of oxalic acid in 0.6 ml of water. The reaction mixture is thereafter stirred for 17 ½ hours at room temperature and diluted with ethyl acetate. The solution is washed neutral with a saturated aqueous solution of sodium chloride, dried over sodium sulphate and concentrated in vacuo. The crude product is chromatographed over silica gel and 91 mg of 2',3'-α-tetrahydrofurane-2'-spiro-17(estra-5(10)-en-3-one) are eluted with a mixture of toluene-/ethyl acetate (95:5). Melting point after crystallisation from acetone/petroleum ether 88°–89° C (yield: 56 mg).

EXAMPLE 12

In a manner analogous to that described in Example 1, 45 g of 3β-hydroxy-androst-5-en-17-one are reacted with a total of 100 ml of 1-chloro-3-diethylaminopropane and lithium to yield the 17a(γ-diethylaminopropyl)androst-5-en-3β,17β-diol, which melts at 144° C after crystallisation from methanol/water. According to the process of Example 2, this compound is first converted into the corresponding methoiodide [17α-(γ-diethyl-methylammoniumpropyl)-androst-5-en-3β,17β-diol-iodide], melting point 281°–283° C (with decomp.) after crystallisation from methanol. The methoiodide is then subjected to thermolysis in the form of the corresponding quaternary base, to yield 2',3'-α-tetrahydrofurane-2'-spiro-17(androst-5-en-3β-ol) which melts at 191°–193° C and is identical to the product obtained in Example 2.

EXAMPLE 13

In a manner analogous to that described in Example 7, a solution of 4.4 g of 3β-hydroxy-androsta-5,9(11)-dien-17-one in 160 ml of absolute tetrahydrofurane is reacted with 1,1 g of lithium and 11 ml of 1-chloro-3-dimethylaminopropane and the reaction mixture worked up. As well as yielding a smaller neutral portion, which consists principally of unreacted starting material, the reaction yields 17α-(γ-trimethylaminopropyl)-androsta-5,9(11)-diene-3β,17β-diol, which is further processed without purification (see Example 14). The 3β-hydroxy-androsta-5,9(11)-dien-17-one used as starting material is obtained as follows:

A mixture of 3.75 g of 3β,17α,21-trihydroxy-pregna-5,9(11)-dien-20-one and 4 g of LiAlH₄ in 300 ml of abs. tetrahydrofurane is refluxed overnight and cooled to 0° C. The excess hydride is decomposed by cautiously adding 10 ml of ethyl acetate and then 50 ml of water. The precipitate is then filtered off with suction and washed twice with tetrahydrofurane and with CH₂Cl₂. The filtrate is concentrated in vacuo and the crude reduction product is dissolved in 60 ml of a 1:1 mixture of pyridine and methanol. This solution is then treated, with stirring, with 30 ml of a 1.2 molar aqueous periodic acid solution in the course of 10 minutes, the temperature rising to 38° C, and stirring is continued for a further 45 minutes. Then 75 ml of a saturated aqueous solution of sodium hydrogen carbonate are added to the reaction mixture and extraction is effected with methylene chloride. The organic extracts are washed successively with 2-normal aqueous hydrochloric acid, 1-normal aqueous NaOH and saturated aqueous solution of sodium chloride until they are neutral, then dried over sodium sulphate and concentrated in vacuo. The very impure 3β-hydroxy-androsta-5,9(11)-dien-17-one is advantageously purified by way of the corresponding 3-acetate in the following manner:

The crude product (2.4 g) is dissolved in 30 ml of a 1:1 mixture of pyridine and acetic anhydride. The solution is left for 6 hours at room temperature and finally evaporated to dryness in vacuo. The crude acetylation product is chromatographed over the 50-fold amount of neutral alumina (activity II), and pure 3β-acetoxy-androsta-5,9(11)-dien-17-one is eluted with toluene and in turn, without further characterisation, hydrolysed for 1 hour under reflux in 18 ml of a 5% methanolic solution of potassium hydroxide. The hydrolysis product is precipitated in pure form from the reaction solution by subsequently adding 25 ml of water. The crystalline product is then filtered off, washed copiously with water, dried in vacuo, and crystallised once from methylene chloride/methanol, to yield 3β-hydroxy-androsta-5,9(11)-dien-17-one with a melting point of 160°–161° C. The same product is also obtained from the identical starting material by conventional NaBiO₃ degradation (in glacial acetic acid).

EXAMPLE 14

3 ml of methyl iodide are added to a solution of 1.69 g of 17α-(γ-trimethylaminopropyl)-androsta-5,9(11)-diene-3β,17-diol in 18 ml of methanol. The reaction mixture is left for 2 hours at room temperature and for 2 hours at −10° C. It is then concentrated to some extent and the crystallised 17α-(γ-trimethylammoniumpropyl)-androsta-5,9(11)-diene-3β,17β-diol-iodide is collected by filtration and dried in vacuo at 60° C. Melting point: 279°–284° C with decomposition.

EXAMPLE 15

A warm solution of 1.5 g of 17α-(γ-trimethylammoniumpropyl)-androsta-5,9(11)-diene-3β,17β-diol-iodide in 15 ml of methanol is diluted with 15 ml of water and 3 ml of 1-normal aqueous NaOH and heated to app. 60° C until a clear solution is obtained. To the reaction mixture are added 30 ml of ethylene glycol and the solvents are slowly distilled off until an internal temperature of app. 185° C is attained, which is then kept for 3 hours. After cooling, the 2',3'-α-tetrahydrofurane-2'-spiro-17[androsta-5,9(11)-dien-3β-ol] crystallises out overnight from the reaction mixture. The crystals are filtered off with suction, washed with a small amount of ethylene glycol and copiously with water and dried to constant weight at 70° C in vacuo. Melting point: 154°–157° C.

EXAMPLE 16

A solution of 2.8 g of 2',3'-α-tetrahydrofurane-2'-spiro-17[androsta-5,9(11)-dien-3β-ol] in 110 ml of toluene is reacted with 25 ml of cyclohexanone and 3.5 g of aluminum isopropylate in a manner analogous to that described in Example 7 and worked up. The resultant crude product is chromatographed through 200 g of silica gel in a gradient column, and 2',3'-α-tetrahydrofurane-2'-spiro-17[androsta-4,9(11)-dien-3-one is eluted with a 9:1 mixture of toluene and ethyl acetate. Melting point: 172°–174° C after crystallisation from ether/pentane.

EXAMPLE 17

A solution of 1.5 g of 2',3'-α-tetrahydrofurane-2'-spiro-17[androsta-4,9(11)-dien-3-one] in 37.5 ml of methanol is reacted with 1.05 g of chloranil in a manner analogous to that described in Example 5, and worked up. The crude product obtained is first filtered through the 10-fold amount of neutral alumina (activity II) in toluene and the eluates are chromatographed through 200 g of silica gel in a gradient column. Pure 2',3'-α-tetrahydrofurane-2'-spiro-17[androsta-4,6,9(11)-trien-3-one] is eluted with a 95:5 mixture of hexane and acetone. Melting point: 117°–118° C after crystallisation from ether/pentane.

We claim:

1. A process for the manufacture of 17-spiro-(2'-oxacyclopentane) compounds of the general formula

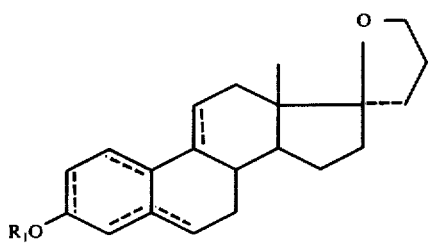

(I)

wherein $R_1$ represents a hydrogen atom or a lower alkyl group, which contain a double bond in 5-position and a methyl group in 10-position, or three double bonds in the positions 1,3 and 5(10), and which can contain an additional double bond in the 9(11)-position, which process comprises reacting a 17-oxosteroid of the general formula

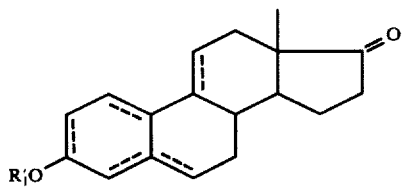

(II)

wherein $R_1'$ represents a hydrogen atom, a lower alkyl group or an acyl group, which contains a double bond in 5-position and a methyl group in 10-position, or three double bonds in the position 1,3 and 5(10), and which can contain an additional double bond in the 9(11)-position, with an organometallic compound of the formula $R_o$—$(CH_2)_3$—M        (III)

wherein M represents a grouping MgX, in which X represents a halogen atom or an alkali metal atom and $R_o$ represents a di-lower alkylamino group, converting, by treatment with a lower alkyl ester of a strong acid, the resultant 17β-hydroxy-17α-(γ-di-lower alkylaminopropyl) compound of the general formula

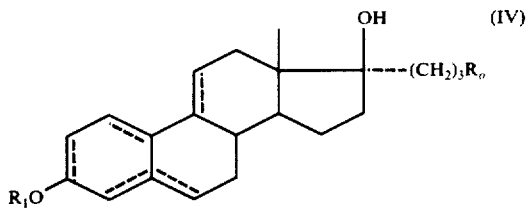

(IV)

wherein $R_1$ and $R_o$ are as defined in formulae (I) and (III), respectively, and which contains a double bond in 5-position and a methyl group in 10-position, or three double bonds in the position 1,3 and 5(10), and which can contain an additional double bond in the 9(11)-position, into the corresponding quaternary tri-lower alkylammonium salt, liberating the corresponding quaternary base with a strong base and heating the latter up to the temperature of decomposition.

2. A process according to claim 1, wherein M in formula III represents lithium.

3. A process according to claim 1, wherein a di-lower alkyl sulphate or a lower alkyl halide is used as lower alkyl ester.

4. A process according to claim 1, wherein an alkali metal hydroxide is used as strong base.

5. A process according to claim 1, wherein the quaternary salt is treated with an equimolar amount of potassium or sodium hydroxide in aqueous solution, ethylene glycol is added, and the mixture is concentrated by distillation until decomposition is complete.

6. 2',3'-α-Tetrahydrofurane-2'-spiro-17[androsta-5,9(11)-dien-3α-ol].

7. A process according to claim 1 for the manufacture of 17β-hydroxy-17α-(γ-di-lower alkylaminopropyl) compounds of the general formula

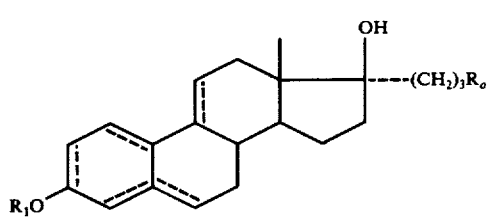

(IV)

wherein $R_1$ represents a hydrogen atom or a lower alkyl group and $R_o$ represents a di-lower alkylamino group, which contain a double bond in 5-position and a methyl group in 10-position, or three double bonds in the positions 1,3 and 5(10), and which can contain an additional double bond in 9(11)-position, and the addition salts thereof, which process comprises reacting a 17-oxosteroid of the general formula

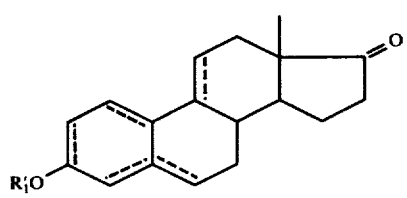

(II)

wherein $R_1'$ represents a hydrogen atom, a lower alkyl group or an acyl group, which contains a double bond in 5-position and a methyl group in 10-position, or three double bonds in the positions 1,3 and 5(10), and which contain an additional double bond in 9(11)-position, with an organometallic compound of the formula $R_o$—$(CH_2)_3$—M        (III)

wherein M represents a grouping MgX, in which X represents a halogen atom or an alkali metal atom, and $R_o$ is as defined hereinabove, and optionally converting the reaction product into an addition salt.

* * * * *